United States Patent [19]

Sagawa et al.

[11] 3,947,429
[45] Mar. 30, 1976

[54] METHOD FOR INHIBITING PREMATURE VULCANIZATION OF DIENE RUBBERS

[75] Inventors: Seiji Sagawa, Hirakata; Tsunehiko Nakagawa, Osaka; Osamu Yoshida, Nishinomiya; Kenjiro Mori, Takarazuka; Junichi Ebisutani, Neyagawa, all of Japan

[73] Assignee: Sumitomo Chemical Company, Limited, Japan

[22] Filed: Feb. 27, 1974

[21] Appl. No.: 446,522

Related U.S. Application Data

[63] Continuation-in-part of Ser. No. 205,368, Dec. 6, 1971, abandoned.

[30] Foreign Application Priority Data

Dec. 29, 1970 Japan.............................. 45-124425

[52] U.S. Cl..... 260/79.5 B; 260/42.14; 260/293.85; 260/780; 260/784
[51] Int. Cl.² .......................................... C08F 9/00
[58] Field of Search............ 260/79.5 B, 42.14, 784, 260/780, 293.85

[56] References Cited
UNITED STATES PATENTS

| | | | |
|---|---|---|---|
| 3,036,980 | 5/1962 | Dunham, Jr. .................... | 260/31.4 |
| 3,513,139 | 5/1970 | Coran............................. | 260/79.5 B |
| 3,640,976 | 2/1972 | Boustany........................ | 260/79.5 B |

*Primary Examiner*—Christopher A. Henderson, Jr.
*Attorney, Agent, or Firm*—Stewart and Kolasch, Ltd.

[57] ABSTRACT

The premature vulcanization of rubber materials is substantially inhibited by incorporating therein a sulfenamide of the formula:

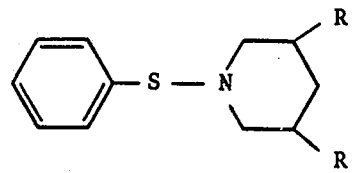

wherein R, which may be the same or different, is alkyl of 1 to 8 carbon atoms. The preferred sulfenamide is N-phenythio-3,5-lupetidine. Said sulfenamide is incorporated into the rubber with or without a conventional vulcanization accelerator and is preferably employed in the form of a powder preparation adsorbed in an inorganic carrier.

1 Claim, No Drawings

METHOD FOR INHIBITING PREMATURE VULCANIZATION OF DIENE RUBBERS

This application is a continuation-in-part of copending application Serial No. 205,368, filed on Dec. 6, 1971 abandoned.

The present invention relates to a method for inhibiting the premature vulcanization of rubber materials. More particularly, it relates to an improved method for inhibiting the premature vulcanization of synthetic rubber materials and also accelerating the vulcanization rate of the said rubber materials. Even more particularly, the invention is concerned with certain compounds which possess an excellent premature vulcanization inhibitory property.

In the manufacture of vulcanized rubber products, the occurrence of local vulcanization as is encountered in some steps for processing unvulcanized rubber materials such as kneading, extruding and calendering is called "premature vulcanization". The prevention of this unfavorable phenomenon is quite important for the manufacture of vulcanized rubber products.

In order to inhibit the premature vulcanization of rubber materials, there has heretofore been proposed the use of a delayed action vulcanization accelerator and/or a premature vulcanization inhibitor. On the other hand, the operations for rubber processing are nowadays performed at an elevated temperature with a high speed, and the appearance of a method for attaining the prevention of premature vulcanization much more effectively and accelerating the vulcanization with a higher rate has thus been desired.

Some sulfenamide compounds have heretofore been employed as late effective vulcanization accelerators but are not satisfactory with respect to scorch time and vulcanization rate. Even when employed together with known premature vulcanization inhibitors such as N-nitrosodiphenylamines and phthalic anhydrides, the prevention of premature vulcanization is insufficient. In addition, this combined use results disadvantageously in the depression of the vulcanization rate and the modulus of the vulcanized rubber product.

As premature vulcanization inhibitors, there have been recently proposed N-(organothio)substituted imides [South African patent 663,072], N-(organothio)-benzimidazolinone compounds [U.S. Pat. No. 3,427,319] and N-(organothio)substituted amines [U.S. Pat. No. 3,382,219; Japanese Pat. No. 29902/1970]. These are satisfactory as to their effect in inhibiting premature vulcanization but still have some defects, such as providing an insufficient vulcanization rate, causing a depression of the modulus in the vulcanized goods, becoming decomposed within a relatively short period of time and the like.

It has now been found certain compounds are quite useful as premature vulcanization inhibitors and, when used with or without conventional vulcanization accelerators, produce a remarkable premature vulcanization inhibition. Particularly notable in the present invention is the fact that the combined use of the said premature vulcanization inhibitor and a conventional vulcanization accelerator shows a higher initial rate of vulcanization than does the sole use of the conventional vulcanization accelerator. In addition, the modulus of the vulcanized rubber product is advantageously increased by the use of the premature vulcanization inhibitors of this invention.

The premature vulcanization inhibitors of this invention comprise sulfenamides having the formula:

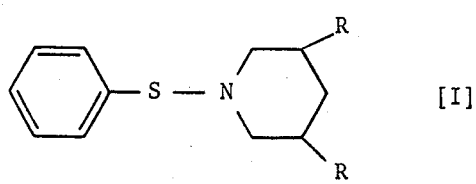

wherein R is alkyl. The two R's may be the same or different.

The term "alkyl" herein is intended to mean an alkyl group having 1 to 8 carbon atoms which may be straight or branched. Thus, specific examples of "alkyl" are methyl, ethyl, propyl, isopropyl, butyl, t-butyl, pentyl, octyl, etc.

The preferred sulfenamide to be employed in connection with this invention is N-phenylthio-3,5-lupetidine. This compound and the related compounds falling within the scope of formula [I] may be produced, for example, by reacting a piperidine compound of the formula:

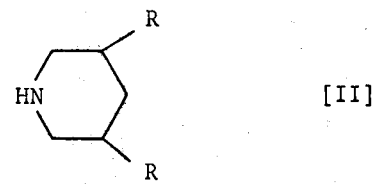

wherein R is alkyl with a mercaptan compound of the formula:

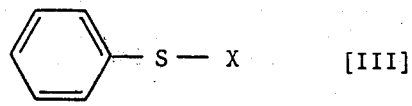

wherein X is halogen (e.g., chlorine or bromine) in the presence of an auxiliary agent (e.g., pyridine, dimethylamine, trimethylamine, sodium carbonate or sodium hydroxide) or an excess amount of the said piperidine compound in an inert organic solvent at a temperature of from 20° to 80°C.

According to the present invention, the sulfenamides [I] are used as premature vulcanization inhibitors for diene rubber materials. The sulfenamides [I] are equally applicable to all rubber materials and exert an excellent premature vulcanization inhibiting effect particularly in synthetic rubbers such as styrenebutadiene rubber (SBR).

The sulfenamides [I] are mostly liquid and can be incorporated as such into rubber materials. As seen with conventional liquid premature vulcanization inhibitors such as N-phenylthiomorpholine and N-phenylthio-t-butylamine, however, the incorporation of the sulfenamides [I] in a liquid form is not favorable because the liquid form causes the rubber materials to slip during processing, thus requiring a long time for completion of the uniform admixture thereof. Thus, the incorporation in powder form is much more preferred. Advantageously, the sulfenamide [I] can be converted with ease into a powdery form, for instance, by admixing with an inorganic solid carrier useful as an inorganic filler such as silica, magnesium carbonate, calcium carbonate or carbon black. As the inorganic solid carrier, the use of one having a smaller particle size and being capable of adsorbing a larger amount of the sulfenamide [I] is preferable. A higher mixing ratio of the sulfenamide [I] to the inorganic solid carrier is preferred but the content of the sulfenamide [I] in the mixture usually does not exceed 50 to 60% by weight.

The amount of the sulfenamide [I] to be incorporated into a rubber material can be varied in a conventional manner with the kind of rubber material, the conditions used for vulcanization, the intended use of the vulcanized product and so on and may usually be from about 0.05 to about 5 parts by weight per 100 parts by weight of the rubber material.

The amounts of sulfur and inorganic filler such as carbon black can also be varied in a known manner depending on the utilization field of the vulcanized product and, in the case of a conventional tire tread, the use of 45 to 55 parts by weight of carbon black and 1 to 4 parts by weight of sulfur is appropriate.

Since the sulfenamide [I] itself possesses a certain vulcanization accelerating effect, it may be used alone in vulcanization processing. It is, however, quite feasible and advantageous to use the sulfenamide [I] together with any vulcanization accelerator, of which preferred examples include N-oxydiethylenebenzothiazole-2-sulfenamide, N-t-butylbenzothiazole-2-sulfenamide, N-cyclohexylbenzothiazole-2-sulfenamide, etc.

The vulcanization temperature may be appropriately selected depending on the kind of rubber material to be processed and is usually from 100° to 150°C.

The sulfenamide [I] produces a prolongation of the scorch time of rubber materials. Even when processed under harsh conditions such as heat treatment, mixing, extruding and calendering, it is effective. The compounds of the invention exert their advantageous effects and properties even when employed with certain amines which are useful as aging inhibitors for shortening the scorch time.

Some embodiments of this invention are illustratively shown in the following Examples wherein parts are by weight.

EXAMPLE 1

Preparation of N-phenylthio-3,5-lupetidine:

In a flask, 3,5-lupetidine (22.9 parts), triethylamine (20.4 parts) and ether (200 parts) are charged, and phenylsulfenyl chloride (27.7 parts) is dropwise added thereto. The resultant mixture is stirred at 30°C for 6 hours. The reaction mixture is filtered to separate the precipitate and the filtrate is distilled to give N-phenylthio-3,5-lupetidine (36 parts by weight). B.P.; 134°C/4 mmHg. $n_D^{25}$ 1.5511.

EXAMPLE 2

Preparation of a powdery composition containing N-phenylthio-3,5-lupetidine:

N-Phenylthio-3,5-lupetidine (50 parts) is mixed uniformly with hydrous silicic acid (50 parts) having a particle size of 16 m$\mu$ and an oil adsorption of 230 g/100 ml by the aid of a mixer to give a powdery composition containing N-phenylthio-3,5-lupetidine.

In a similar manner, other sulfenamides [I] are produced and formulated into a powdery composition.

The effect for preventing the premature vulcanization of rubber materials was tested as follows:

The 50% powdery composition of the sulfenamide [I] prepared as in Examples 1 and 2 was incorporated into styrene-butadiene rubber (SBR), and the resultant mixture was subjected to a conventional standard vulcanization test. The measured premature vulcanization inhibiting properties are shown in Table 1 wherein $t_{90}$ indicates the necessary time (min.) in which the torque value decreases from its maximum value to a value less than 1/10 of $R_{max} - R_{min}$ in the rheometer curve, $t_{10}$ indicates the necessary time (min.) in which the torque value increases from its minimum value to a value greater than 1/10 of ($R_{max} - R_{min}$) in the rheometer curve and ($t_{90} - t_{10}$) represents the necessary time from the beginning to the end of the vulcanization, i.e., the initial rate of vulcanization, $R_{max}$ and $R_{min}$ being respectively the maximum torque value and the minimum torque value measured.

TABLE 1

| Composition No. | | 1 | 2 | 3 | 4 | 5 | 6 |
|---|---|---|---|---|---|---|---|
| SBR No. 1500 | | 100 | 100 | 100 | 100 | 100 | 100 |
| HAF carbon black | | 50 | 50 | 50 | 50 | 50 | 50 |
| Process oil | | 9 | 9 | 9 | 9 | 9 | 9 |
| Stearic acid | | 3 | 3 | 3 | 3 | 3 | 3 |
| Zinc flowers (ZnO) | | 5 | 5 | 5 | 5 | 5 | 5 |
| Sulfur | | 2 | 2 | 2 | 2 | 2 | 2 |
| N-t-Butylbenzothiazole-2-sulfenamide | | 1 | 1 | 1 | 1 | 1 | 1 |
| Premature vulcanization inhibitor No. | I (50% pulverized) | — | 1.0 | — | — | — | — |
| | II (do.) | — | — | 1.0 | — | — | — |
| | III (do.) | — | — | — | 1.0 | — | — |
| | IV (liquid) | — | — | — | — | 0.5 | — |
| | V (Santogard PVI) | — | — | — | — | — | 1.0 |
| Test results (min.) | Scorch test by Mooney plastometer (135°C, ML$_5$) | 21 | 31 | 34 | 28.5 | 32 | 41 |
| Rheometer test (150°C) | Maximum torque value (kg.cm) | 48 | 47 | 47 | 48 | 46 | 54 |
| | Vulcanization time to 90 % ($t_{90}$) (min.) | 29 | 28 | 33 | 28 | 29 | 30 |

TABLE 1-continued

| Composition No. | 1 | 2 | 3 | 4 | 5 | 6 |
|---|---|---|---|---|---|---|
| Initial rate ($t_{90} - t_{10}$) (min.) | 16 | 9 | 9.5 | 9 | 11 | 12.0 |

Note: Premature vulcanization inhibitor I, N-phenylthio-3,5-dimethylpiperidine; premature vulcanization inhibitor II, N-cyclohexylthio-3,5-dimethylpiperidine; premature vulcanization inhibitor III, N-(p-chlorophenylthio)-2-methylpiperidine; premature vulcanization inhibitor IV, N-phenylthiomorpholine (disclosed in U.S. Pat. No. 3,382,219); premature vulcanization inhibitor V, Santogard PVI (trademark of Monsanto Chemical) having the formula,

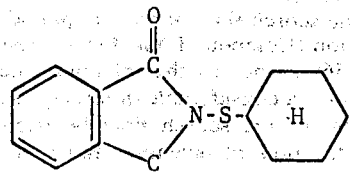

disclosed in South African Pat. No. 663,072).

The unexpected and advantageous premature vulcanization inhibiting properties of N-phenylthio-3,5-dimethylpiperidine as compared with closely related prior art compounds are shown in the following Tables. The tests were conducted in the same manner as indicated above and $t_{90}$, $t_{10}$, ($t_{90} - t_{10}$), $R_{max}$ and $R_{min}$ all have the same meanings as recited above. Each test compound was incorporated into a styrene-butadiene synthetic rubber (SBR No. 1500), and the resultant composition was subjected to a conventional standard vulcanization test.

| Test compound No. | Structure |
|---|---|
| 1 | 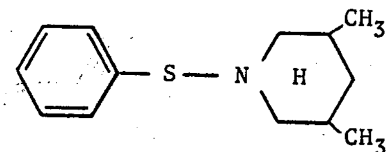 |
| 2 | 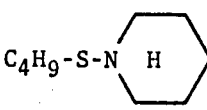 |
| 3 | 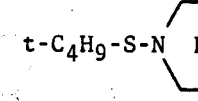 |
| 4 | 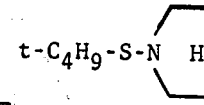 |
| 5 | 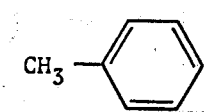 |
| 6 | 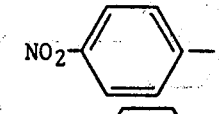 |
| 7 | 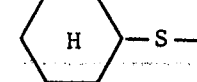 |

The results were as follows:

Table 2

| Composition No. | | | 1 | 2 | 3 | 4 | 5 | 6 | 7 | 8 |
|---|---|---|---|---|---|---|---|---|---|---|
| SBR No. 1500 | | | 100 | 100 | 100 | 100 | 100 | 100 | 100 | 100 |
| HAF carbon black | | | 50 | 50 | 50 | 50 | 50 | 50 | 50 | 50 |
| Process oil | | | 9 | 9 | 9 | 9 | 9 | 9 | 9 | 9 |
| Stearic acid | | | 3 | 3 | 3 | 3 | 3 | 3 | 3 | 3 |
| Zinc flowers (ZnO) | | | 5 | 5 | 5 | 5 | 5 | 5 | 5 | 5 |
| Sulfur | | | 2 | 2 | 2 | 2 | 2 | 2 | 2 | 2 |
| N-t-butylbenzothiazole-2-sulfenamide | | | 1 | 1 | 1 | 1 | 1 | 1 | 1 | 1 |
| Premature vulcanization inhibitor, Compound No. | 1 | | — | 1.0 | — | — | — | — | — | — |
| | 2 | | — | — | 1.0 | — | — | — | — | — |
| | 3 | | — | — | — | 1.0 | — | — | — | — |
| | 4 | | — | — | — | — | 1.0 | — | — | — |
| | 5 | | — | — | — | — | — | 1.0 | — | — |
| | 6 | | — | — | — | — | — | — | 1.0 | — |
| | 7 | | — | — | — | — | — | — | — | 1.0 |
| Test results | Scorch test by Mooney plastometer (135°C, $ML_5$) (min.) | | 21 | 31 | 25 | 26 | 25 | 28 | 27 | 24 |
| | Rheometer test (150°C) | Maximum torque value (kg.cm) | 48 | 47 | 48 | 48 | 47 | 46 | 47 | 24 |
| | | Vulcanization time to 90% ($t_{90}$) (min.) | 29 | 28 | 30 | 30 | 29 | 29 | 31 | 27 |
| | | Initial rate ($t_{90} - T_{10}$) (min.) | 16 | 9 | 14 | 14 | 15 | 12 | 13 | 10 |

From these tests it can be seen that Compound No. 1 has a much superior premature vulcanization inhibiting property as compared to the structurally related compounds 2-7.

Additional tests conducted in the same manner with the following compounds gave results shown in Table 3.

Test compound

| No. | Structure |
|---|---|
| 1 | phenyl—S—N(H)(piperidine with 2,6-di-CH₃) |
| 8 | cyclohexyl—S—N(H)(piperidine with 2-CH₃) |
| 9 | cyclohexyl—S—N(H)(piperidine with 2-CH₃, 5-CH₃) |
| 10 | cyclohexyl—S—N(H)(piperidine with 2-CH₃, 6-CH₃) |
| 11 | cyclohexyl—S—N(H)(piperidine with 2,6-di-CH₃) |

Table 3

| | | | | | | |
|---|---|---|---|---|---|---|
| SBR No. 1500 | 100 | 100 | 100 | 100 | 100 | 100 |
| HAF carbon black | 50 | 50 | 50 | 50 | 50 | 50 |
| Process oil | 9 | 9 | 9 | 9 | 9 | 9 |
| Stearic acid | 3 | 3 | 3 | 3 | 3 | 3 |
| Zinc flowers (ZnO) | 5 | 5 | 5 | 5 | 5 | 5 |
| Sulfur | 2 | 2 | 2 | 2 | 2 | 2 |
| N-t-butylbenzothiazole-2-sulfenamide | 1 | 1 | 1 | 1 | 1 | 1 |
| Premature vulcanization inhibitor, Compound No. 1 | — | 1.0 | — | — | — | — |
| 8 | — | — | 1.0 | — | — | — |
| 9 | — | — | — | 1.0 | — | — |
| 10 | — | — | — | — | 1.0 | — |
| 11 | — | — | — | — | — | 1.0 |

| Test Results | | | | | | | |
|---|---|---|---|---|---|---|---|
| Scorch test by Mooney plastomer (135°C, ML₅) (min.) | | 20.5 | 32 | 28 | 28 | 28 | 27 |
| Rheometer test (150°C) | Maximum torque value (kg.cm) | 48 | 47 | 48 | 47 | 48 | 48 |
| | Vulcanization time to 90% (t₉₀) (min.) | 29 | 28 | 28 | 29 | 28 | 30 |
| | Initial rate (t₉₀-t₁₀) (min) | 16.5 | 8.5 | 12 | 12 | 12.5 | 13 |

From these results it is clear that N-phenylthio-3,5-dimethylpiperidine (N-phenylthio-3,5-lupetidine), i.e., Compound No. 1, shows an unexpectedly larger scorch delay effect and a higher initial rate of vulcanization and, therefore, is a much more valuable premature vulcanization inhibitor than the closely related cyclohexyl sulfenamides of the prior art.

These conclusions are drawn from the above results and the following facts. As noted above, the main purpose of a premature vulcanization inhibitor is to prevent the occurrence of local vulcanization in the course of processing unvulcanized rubber materials. This prevention effect is represented by the scorch time. From a practical viewpoint, the scorch time should be about 20 minutes or more. If the scorch time is less than this amount of time, the processing safety is inferior, and such a compound is not practically utilizable as a premature vulcanization inhibitor. On the other hand, it is desired that, if and when vulcanization is once started, it proceed as quickly as possible. Hence, a higher initial rate of vulcanization is preferred.

These two desirable properites are somewhat inconsistent, and most conventional premature vulcanization inhibitors having a larger scorch delay effect show a lower initial rate of vulcanization. In Table 3 the increase of the scorch time of the compound of the present invention (Compound No. 1) with respect to the control is 56%, whereas that of compounds 8-11 is 31-36%. Thus, a considerable difference is seen in the improvement of the scorch time between the compounds of the present invention and very closely related prior art compounds, constituting a novel and unexpected result. Furthermore, a remarkable difference is seen in the improvement of the initial rate of vulcanization wherein the elevation of the initial rate of the inventive compound with respect to the control is 48%, whereas that of the related prior art compounds is only 21-27%. Thus, it should be particularly noted that, contrary to the general tendency known in the art, the compounds of the invention exhibit the longest scorch time and the highest initial rate of vulcanization.

The invention being thus described, it will be obvious that the same may be varied in many ways. Such variations are not to be regarded as a departure from the spirit and scope of the invention and all such modifications are intended to be included within the scope of the following claims.

We claim:

1. A vulcanizable composition comprising a diene rubber and N-phenylthio-3,5-lupetidine.

* * * * *